United States Patent
Montoya-Olvera et al.

(10) Patent No.: US 6,504,067 B1
(45) Date of Patent: Jan. 7, 2003

(54) PROCESS TO OBTAIN XANTHOPHYLL CONCENTRATES OF HIGH PURITY

(75) Inventors: Ricardo Montoya-Olvera, Nuevo León (MX); Juan-Roberto Elizondo-Mireles, Nuevo León (MX); Carlos-Javier Torres-Gómez, Nuevo León (MX); José-Odon Torres-Quiroga, Nuevo León (MX)

(73) Assignee: Industrial Organica S.A. DE C.V., Monterrey (MX)

(*) Notice: Subject to any disclaimer, the term of this patent is extended or adjusted under 35 U.S.C. 154(b) by 0 days.

(21) Appl. No.: 09/449,229

(22) Filed: Nov. 24, 1999

(51) Int. Cl.$^7$ ................................................ C07C 35/21
(52) U.S. Cl. ....................................................... 568/816
(58) Field of Search .......................................... 568/816

(56) References Cited

U.S. PATENT DOCUMENTS

| | | | |
|---|---|---|---|
| 3,523,138 A | * 8/1970 | Grant ........................ | 568/816 |
| 3,997,679 A | * 12/1976 | Salkin ....................... | 568/816 |
| 5,382,714 A | 1/1995 | Khachik ..................... | 568/834 |
| 5,523,494 A | 6/1996 | Torres-Cardona et al. .. | 568/834 |
| 5,648,564 A | 7/1997 | Ausich et al. .............. | 568/834 |
| 5,780,693 A | * 7/1998 | Bernhard ................... | 568/816 |
| 5,876,782 A | * 3/1999 | Sas ........................... | 568/816 |
| 5,959,138 A | 9/1999 | Torres-Cardona et al. .. | 560/190 |
| 5,973,211 A | * 10/1999 | Rodriguez ................. | 568/816 |
| 5,997,922 A | 12/1999 | Torres-Cardona et al. .. | 426/250 |
| 5,998,678 A | * 12/1999 | Virgili ....................... | 568/816 |

FOREIGN PATENT DOCUMENTS

JP          57-133160     * 8/1982

* cited by examiner

*Primary Examiner*—Michael L. Shippen
(74) *Attorney, Agent, or Firm*—Abelman, Frayne & Schwab

(57) ABSTRACT

An industrial process to obtain xanthophyll concentrates of high purity from plant extracts, comprising: refining the plant extracts by treating them with a diluted alkali, followed by treating them with a diluted organic or inorganic acid in order to eliminate impurities and undesirable components and obtaining a refined extract; saponifying the refined extract by means of a strongly alkali aqueous solution; treating the diluted saponified mass with a dilute organic or inorganic acid to adjust the pH to a value from 4 to 7, in order to separate a xanthophylls concentrate; and removing any remaining impurities by extracting them by means of hexane.

23 Claims, No Drawings

PROCESS TO OBTAIN XANTHOPHYLL CONCENTRATES OF HIGH PURITY

BACKGROUND OF THE INVENTION

1. Field of the Invention

This invention refers to an industrial process to obtain xanthophyll concentrates of high purity from sources of plant origin, suitable for human or animal consumption and, more specifically, to a process of refining plant extracts by means of treatment with dilute alkali, followed by treatment with a dilute acid.

2. Description of the Related Art

Carotenoids are natural pigments that are widely found in vegetable and animal species. It comprises the family of Carotenes, which are hydrocarbon carotenoids such as: β-carotene and lycopene, and the hydroxy or oxy carotenoids, such as lutein, zeaxanthin, capsanthin, capsorrubin, astaxanthin, bixin, crocetin and others.

Carotenoids are widely produced on a large scale in nature, in plants (leaves, flowers and fruits), microalgae, fungii and bacteria.

Since animals do not have the capacity to biosynthesize carotenoids, they can only take advantage of the carotenoids found in natural sources for different purposes, such as, acquiring color (birds and fish) or to accomplish metabolic and reproductive functions (crustaceans), among others.

In recent years, it has been widely documented by scientific evidence that some carotenoids, for example, lutein and zeaxanthin among others, provide beneficial effects to the human being. It has been widely shown that their natural antioxidant properties reduce the risk of tissue degenerative diseases such as cancer, and also help to prevent macular degeneration in adults.

An abundant and varied diet composed of fresh fruits and vegetables should be generally regarded as ample enough to satisfy the carotenoid requirements of a human being. However, nowadays an unbalanced and deficient human diet lacks the required amounts of lutein, zeaxanthin and other carotenoids. It is for such reason that it has become very desirable to find alternate natural sources of carotenoids having a high concentration and purity.

Lutein and zeaxanthin occur widely in nature in fresh vegetables like spinach, broccoli, green peas, brussel sprouts, squash as well as in fresh fruits like mangoes, papaya, peaches, oranges, etc., and also in alfalfa.

In some vegetables, the xanthophylls are found in their free form. However, in most instances they are found as diesters of fatty acids, such as myristic, lauric and palmitic acids. In order to assimilate those xanthophylls, the organism hydrolyses the diesters so that absorption occurs and enables the organism to metabolize them.

In the last few decades there has been an increased worldwide production of marigold (*Tagetes erecta*). Marigold flowers contain a high concentration of xanthophylls, predominantly lutein, and some zeaxanthin. Such source of xanthophylls is widely used by the feed industry in order to obtain a good pigmentation in broilers and egg yolks.

Only recently has a growing demand developed in order to supplement the human diet with such xanthophylls. For such reason, it is timely to develop processes with economic feasibility to concentrate and purify the xanthophylls for human consumption, such as lutein and zeaxanthin, among others.

In the research works of Tcyczkowski and Hamilton, reported in *Poultry Science* 70(3):651–654, 1991, they developed a laboratory analytical technique to isolate and crystallize lutein (and zeaxanthin) from a saponified marigold extract, by using organic solvents, that it is not viable to be carried out at an industrial process level. Furthermore, such solvents can leave noxious residues which are trapped or occluded in the crystals.

The use of solvents like methanol or halogenated organic solvents like dichloromethane or dichloroethane as in U.S. Pat. No. 5,382,714, of Khachik et al, 1995, implies crystallization and recrystallization processes, low temperatures, etc., in order to obtain highly pure lutein crystals. The use of solvents with a high level of toxicity requires an expensive and elaborated equipment to handle such solvents, and may result non feasible at an industrial production level.

In U.S. Pat. No. 5,648,564 granted to Ausich et al in 1997, they "surprisingly" found that upon the saponification of the marigold oleoresin with an aqueous alkali diluted with propylene glycol, lutein crystals appeared. It is known to people skilled in the art that the fatty acid diesters of xanthophylls are soluble in non-polar aliphatic solvents that have a high affinity for fats, such as aliphatic solvents (hexane, pentane, etc.). Upon hydrolyzing the xanthophylls, they become insoluble in aliphatic solvents and/or water, but they are highly soluble in polar solvents, such as ketones, alcohols, chlorinated solvents etc. It is known also, that lutein and zeaxanthin occur always as minute crystals during the aqueous phase saponification reaction of the marigold oleoresin, unless it is carried out in the presence of polar solvents. Such occurrence is widely recognized in the art when the hydrolysis of the xanthophyll diesters is carried out in a non-polar media (alkaline water or alkaline water plus propylene glycol).

In the process of the present invention, we have been able to obtain xanthophyll concentrates having a high purity, in a simple manner, using non toxic reagents that are not dangerous to handle, and without requiring expensive equipment or costly low temperature crystallization steps. Starting from the principle that by employing the same and only solvent (hexane) that is used in the industry to obtain the xanthophyll diesters extraction from the plant material (oleoresin), followed by a simple procedure by which the xanthophylls become insoluble in said solvent, the impurities and all the undesired material (all of them soluble in hexane) are separated or removed with the use of the same hexane solvent, producing a xanthophyll concentrate of high purity.

As it will be explained hereinafter in further detail, by this process lutein and zeaxanthin concentrates are obtained having a high degree of purity when Tagetes oleoresin is used as the raw material. By the process of the present invention, capsanthin and capsorrubin concentrates of high purity are also obtained when Capsicum oleoresin is used as the raw material.

This is a novel process wherein the impurities are eliminated or removed in the different stages, while the xanthophylls concentrate is enriched after each stage. In all other known processes or methods, the xanthophylls are selectively extracted from the xanthophylls containing mass by means of different solvents that commonly are expensive or dangerous, or use costly low temperature crystallization and recrystallization processes, wherein pigment loss may occur.

This process to concentrate and purify xanthophylls like lutein, zeaxanthin, capsanthin and capsorrubin starting from botanical extracts, is surprisingly efficient, economical and clean.

SUMMARY OF THE INVENTION

The first step of this process comprises refining the oleoresin from which several undesirable materials such as free fatty acids, gums, waxes, sterols, phosphatides, lipids, clorophylls, volatile compounds etc., are removed. This refining operation is carried out in a first step by a gentle treatment of the oleoresin with a dilute alkali and separating the impurities by means of a centrifugal machine. After thoroughly rinsing and separating the aqueous phase from the oleoresin, a treatment with a dilute acid is carried out. The oleoresin is thoroughly rinsed again, and the aqueous phase is removed by centrifugation.

In the enriched oleoresin obtained from the previous step, the xanthophylls are found as diesters of fatty acids. The second step of the process comprises hydrolyzing the diesters in order to obtain free xanthophylls. The diester hydrolysis is carried out with an aqueous alkali, in the presence of emulsifiers. This reaction is performed without the use of alcohols or organic solvents.

The third step of this process comprises diluting the saponified mass with water and reducing the pH of the concentrate dispersion by adjusting it with a diluted acid until a slight acid reaction is obtained, and a clear separation of phases occur. The two phases are separated by centrifuging or decanting operations. The supernatant organic phase contains free fatty acids and minute xanthophyll crystals. The aqueous phase is discarded and the enriched xanthophyll concentrate is rinsed several times to remove any acid traces as well as the salts formed during the acidification. The enriched xanthophyll concentrate is separated by means of a centrifuge or by decanting, followed by a treatment to remove water traces by filtering and drying under vacuum.

In the fourth step the dried xanthophyll concentrate is extracted several times with an aliphatic hydrocarbon selected from among hexane, pentane and heptane, with hexane being preferred under intense agitation in a closed vessel, in order to remove all the free fatty acids as well as any non-polar impurities that might remain.

In the fifth step, the hexane, for example, is easily separated by decanting or centrifuging operations. The hexane is then recovered by evaporation in a closed system. The residue obtained after the evaporation of the hexane consists mainly of free fatty acids, carotenes, etc.

In the sixth step, the enriched xanthophyll concentrate is freed from any hexane traces by gentle warming under high vacuum and swept with a nitrogen stream. This highly pure xanthophyll concentrate is ready to be formulated with suitable carriers to obtain a premix; or to be coated with gelatin or any other microcapsule coating material; or to be dispersed in edible oil.

The xanthophyll concentrate has a concentration of total carotenoids above 98%, with a xanthophyll concentration above 95%. If higher purity is required, it can be attained by repeating the fourth, fifth and sixth steps.

It is therefore an object of the present invention, to provide a process to obtain xanthophyll concentrates having a high purity, starting from plant extracts (oleoresins).

It is another object of the present invention, to provide a process to obtain highly pure xanthophyll concentrates, which includes a refining step in order to remove a substantial amount of impurities for subsequent treatment.

It is still another object of the present invention, to provide a process to obtain highly pure xanthophyll concentrates of the type mentioned previously, by means of refining, saponifying, acidifying and extracting with an aliphatic hydrocarbon.

It is yet a further object of the present invention, to provide a process to obtain highly pure xanthophyll concentrates.

It is yet a further object of the present invention to provide a process in which the treatment with acid, alkaline solutions, neutral and non polar solutions and hexane, guarantees a high degree of purity in the product obtained, free from traces of reagents or solvents which pose a health risk.

These and other objects and advantages of the process of the present invention will become apparent to those persons having ordinary skill in the art, as can be seen from the following detailed description of the invention, and after examining the referenced examples pertaining to this process.

DETAILED DESCRIPTION OF THE INVENTION

The process of the present invention is to obtain xanthophyll concentrates of high purity.

The first step of the process is an oleoresin refining operation in which many of the undesirable components are eliminated, such as free fatty acids, gums, waxes, phoshatides, lipids, sterols, chlorophylls and volatile compounds, and an enriched and deodorized oleoresin is obtained.

The plant extract employed in the first process step is selected from the group consisting of marigold oleoresin (*Tagetas erecta*), red chili or paprika oleoresin (*Capsicum annum*), saponified and isomerized marigold oleoresin (*Haematococcus pluvialis*), an extract of the fruit *Lycium barbarum*, extracts of *Bixa orellana*, extracts of *Crocus sativus*, or a combination thereof.

This oleoresin refining step is carried out by an alkaline treatment by means of a dilute alkaline solution, such as KOH, NaOH, $CaCO_3$, $Na_2CO_3$, $K_2CO_3$, or a combination thereof, having a concentration in relation to the acid value of the oleoresin.

A molar ratio of acid:alkali of between about 1:0.5 to 1:1, preferably 1:0.5 is employed, with the alkaline treatment requiring intense agitation of the mixture at a temperature from about 25° C. to 90° C., preferably at about 40° C for a period of about 1 to 240 minutes, preferably about 30 minutes. Immediately after this treatment, a two phase separation is performed by centrifugal means. The alkaline treatment is followed by adding a dilute solution of an inorganic or an organic acid, such as phosphoric acid, acetic acid, citric acid, etc., in a ratio of about 0.2 to 1.5% by volume, preferably about 1%.

The dilute acid treatment requires intense agitation of the mixture at a temperature from about 25° to 90° C., preferably about 40° C. for a period of about 1 to 240 minutes, preferably about 30 minutes. The acid treatment is followed by a separation of the two phases by centrifugation.

The second step of the process involves an aqueous hydrolysis of the refined oleoresin that has been defatted, degummed and deodorized. The oleoresin is treated with a strong aqueous alkaline solution, containing an amount of alkali of about 20% to 60%, preferably about 45% by weight based on the weight of the refined oleoresin, in the presence of sanitary emulsifiers and antioxidants, such as sorbitan polyethoxylated ethers or esters, citrates, etc. The reaction mixture is kept under agitation at a temperature from about 40° C. to 120° C., preferably about 90° C., for a time from about 1 to 48 hours, preferably about 8 hours, until complete hydrolysis of the diesters has occurred. It is pertinent to observe that in this saponification reaction, no alcohol, or organic solvent or any mixture thereof is used as the reaction media, in clear contrast with the processes disclosed in U.S. Pat. Nos. 5,382,714 and 5,648,564.

In the aqueous saponification of the oleoresin, minute crystals of xanthophylls are formed without requiring a crystallization operation or without the need of lowering the temperature, as pointed out in U.S. Pat. No. 5,382,714.

When the saponification has been completed, all of the xanthophylls present are in their free form. The reaction mass is cooled down, lowering the temperature to about 40° C. to 60° C., preferably to about 50° C.

The saponified mass is diluted with water in a soap:water ratio of about 1:1 to 1:5, preferably to a ratio of about 1:3 and is agitated for a period of 30 minutes.

The diluted refined saponified oleoresin is acidified to a pH value from about 4 to 7, preferably about 5, by means of a water-diluted acid, such as phosphoric, acetic or citric acid, and is agitated for a period of about 60 minutes. During the acid addition, no temperature increase is noticed. This pH adjustment produces a clean separation of the two phases. The aqueous phase is discarded, and the organic phase is rinsed several times with warm water until a neutral pH is obtained and there are no more salts or polar impurities present.

The enriched xanthophyll concentrate is filtered and centrifuged, and then dried under vacuum at about 5 to 26 inches of mercury, preferably at about 24 inches of mercury, at a temperature from about 40° C. to 90° C., preferably at about 50° C., by means of a nitrogen stream, until the moisture content is less than about 10%.

The enriched xanthophyll concentrate is then extracted with an aliphatic hydrocarbon, such as hexane, heptane, or pentane, with hexane being preferred, employing a concentrate: hexane ratio of from about 1:1 to 1:10, preferably about 1:8, in a closed vessel with intense agitation. This operation is carried out several times until all the non-polar impurities such as free fatty acids and their soaps, or any other hexane soluble impurities that might be present, have been extracted. The hexane extractions are carried out at a temperature from about 25° C. to 60° C., preferably about 40° C., for a period from about 1 minute to 240 minutes, preferably about 30 minutes, at atmospheric pressure. After agitation, the xanthophyll concentrate is allowed to settle down for about 1 to 4 hours, preferably about 2 hours.

It is necessary to carry out several extractions until the hexane shows no coloration and leaves no residue upon evaporation. Generally, it takes from about 2 to 10 extractions, preferably about 6.

It is important to point out that the xanthophylls solubility in hexane is nil, and whatever amount which could be present in the hexane is recovered upon recycling. The separation of the hexane from the xanthophyll concentrate is made by decanting and further centrifugal filtration. The hexane is recovered by distillation, and the residue is eliminated.

The xanthophyll concentrate of high purity is dried in a low-pressure chamber provided with a nitrogen stream at a temperature from about 25° C. to 60° C., preferably at about 50° C.

The highly pure xanthophyll concentrate is ready to be standardized, stabilized and formulated in a premix, or microencapsulated, or dispersed in edible oil.

The following examples are provided to illustrate the present invention, and should not be limitative of the scope of this novel process.

EXAMPLE NO. 1

Refining 400 kgs of marigold oleoresin having a concentration of 90,000 ppm (AOAC) and an acidity of 12% were loaded into a suitable reactor provided with agitation and prepared to apply heat or cold water through a jacket. The temperature of the oleoresin was raised to 40° C. under a slow agitation; 400 kgs of a diluted solution having a concentration of 2.5% of $Na_2CO_3$ were added and the mixture was stirred for a period of 5 minutes. Two phases were immediately separated by means of a centrifugal machine. The water phase was discarded, and the oleoresin was returned to the reactor with agitation; 400 kgs of a water-diluted phosphoric acid solution having a concentration of 1% by weight were added, and the mix was thoroughly stirred during 5 minutes. The two phases are separated by a centrifugal machine, the aqueous phase was discarded, and 285 kgs. of refined oleoresin were obtained.

Saponification

The refined oleoresin was loaded into the reactor, and while maintaining the oleoresin under agitation, 120 kgs of an aqueous solution containing 45% of KOH were added slowly and the temperature increased to 90° C. The reactor was closed, and a nitrogen atmosphere layer was provided. This condition was maintained for a period of 8 hours, causing a hydrolysis with a saponification above 95.5% after such period.

PH Adjustment

After a complete saponification occurred, 1,200 kgs of water at room temperature were added under agitation, the temperature was reduced and maintained at 50° C., and the mixture was agitated for one hour. after such reaction period 100, kgs of a water-diluted acetic acid having with a concentration of 25% were added in order to adjust the pH of the mixture to a value of 5, and once such pH was attained, the agitation was continued for another additional 30 minutes.

The water phase was eliminated under no agitation at the bottom of the reactor, and several water rinses were performed until the pH of the water was neutral and all acid residues and salts were removed. The xanthophyll concentrate was dried under vacuum obtaining 171 kgs of concentrate having a moisture content below 8%.

Hexane Extraction

The xanthophyll concentrate (171 kgs) was successively extracted 5 times by means of 1,100 kgs. of hexane each time. The hexane and the solid concentrate were separated by means of a vacuum filter or by means of a filter centrifuge. The hexane traces were removed by means of a nitrogen stream at 50° C. in a reduced atmosphere chamber.

The xanthophyll concentrate obtained was as follows:

Weight 9.100 kgs

Total xanthophylls (AOAC) 870,000 mg/kg

Purity degree lutein+zeaxanthin 97%

Moisture (Karl Fischer) 8%

As can be observed in this example, a highly pure (HPLC) xanthophyll concentrate was obtained due to the sequential elimination of impurities or undesirable components, starting from the raw material until the xanthophyll concentrate of high purity was obtained. The total xanthophyll loss in the process was only 5.5%. In this example 94.5% of the original xanthophylls was recovered.

EXAMPLE NO. 2

Refining 100 kgs. of marigold oleoresin having a concentration of 120,000 ppm (AOAC) and an acid content of 14%, were loaded into a reactor with agitation and the temperature was increased to 40° C.

100 kgs. of a water-diluted solution containing 2.9% by weight of $Na_2CO_3$ were added and the mixture was agitated for 5 minutes. After the agitation is stopped, the two phases were separated by a centrifugal machine and the aqueous phase discarded.

The oleoresin phase was loaded back into the reactor and 100 kgs of a water-diluted solution containing 1% of phosphoric acid were added. The mixture was agitated for 5 minutes and then transferred into a centrifuge, wherein the two phases were separated. The aqueous phase was discarded, and 71 kgs. of refined oleoresin were obtained.

Saponification

The refined oleoresin was loaded into the reactor and 30 kgs of water solution containing 45% by weight of KOH were added under agitation. The temperature was increased to 90° C. and such conditions were maintained for a period of 8 hours. The hydrolysis performed at the oleoresin was above 95%.

PH Adjustment

After complete saponification was obtained, 300 kgs of water at room temperature were added and the temperature controlled at 50° C., while the agitation was continued. After one hour of agitation, 25 kgs. of a water-diluted acetic acid solution having a concentration of 25% by weight were added until a pH of 5 was reached. The agitation was maintained for additional 30 minutes, and then stopped. The aqueous phase was separated and discarded, and the supernatant layer was rinsed several times with water until a neutral pH was obtained.

The xanthophyll concentrate was filtered in a vacuum filter or separated by a centrifuge, and then dried under a nitrogen stream in a chamber at reduced pressure, and at a temperature of 50° C.

The xanthophyll concentrate of high purity obtained was as follows:

| | |
|---|---|
| Weight | 13.4 kgs |
| Total xanthophylls | 845,000 mg/kg |
| Purity, lutein + zeaxanthin (HPLC) | 96.5% |
| Moisture (Karl Fischer) | 10% |

As can be observed in this example a high purity (HPLC) xanthophyll concentrate was obtained, due to the fact that all of the impurities and undesirable components of the oleoresin were successfully separated in the sequenced steps of the process. In this example 93.85% of the original xanthophyll content was recovered, with a carotenoid loss of only 6%.

While in this example, as well as in the previous one, hexane was the solvent employed, other aliphatic hydrocarbon solvents, such as pentane or heptane, can be used to obtain similar beneficial results.

We claim:

1. A process to obtain a refined xanthophyll concentrate starting from plant extracts or oleoresins, comprising: refining the plant extract or oleoresin by a treatment with a diluted aqueous alkaline solution forming a first oleoresin phase and a first aqueous phase containing impurities; separating the first oleoresin phase from the first aqueous phase containing impurities; treating the first oleoresin phase with a diluted aqueous organic or inorganic acid; forming a second oleoresin phase and a second aqueous phase containing impurities; and separating the second oleoresin phase from the second aqueous phase containing impurities to obtain a refined xanthophyll concentrate.

2. A process according to claim 1, wherein the plant extract is selected from the group consisting of marigold oleoresin (*Tagetes erecta*); red chili or paprika oleoresin (*Capsicum annum*); *Haematococcus pluvialis* extract; extract of the fruit of *Lycium barbarum;* extracts of *Bixa orellana;* extracts of *Crocus sativus;* or an extract that is a mixture thereof.

3. A process according to claim 1, wherein the diluted alkali is selected from the group consisting of an alkaline metal hydroxide, an alkaline-earth metal hydroxide, an alkaline metal carbonate, or an alkaline-earth metal carbonate.

4. A process according to claim 1, wherein the alkali present has a molar ratio with respect to the acidity of the plant extract of from about 1:0.5 to 1:1.

5. A process according to claim 1, wherein the inorganic or organic acid is selected from the group consisting of phosphoric acid, acetic acid, and citric acid.

6. A process according to claim 1, wherein the organic or inorganic acid has a concentration from about 0.2 to 1.5% by volume.

7. A process according to claim 1, further comprising saponifying the refined xanthophyll concentrate with a strongly alkaline aqueous solution to obtain a saponified refined xanthophyll concentrate.

8. A process according to claim 1, further comprising saponifying the refined xanthophyll concentrate with a strongly alkaline aqueous solution to obtain a saponified refined xanthophyll concentrate, and treating the saponified refined xanthophyll concentrate with an organic or inorganic acid, adjusting the pH between 4 and 7, forming a third acidic refined xanthophyll concentrate and a third aquous phase containing impurities; separating the third acidic refined xanthophyll concentrate from the third aqueous solution; eliminating any excess of acid and any salts formed, from the third acidic refined xanthophyll concentrate and separating a purified refined xanthophyll concentrate.

9. A process according to claim 1, further comprising saponifying the refined xanthophyll concentrate with a strongly alkaline aqueous solution to obtain a saponified refined xanthophyll concentrate; treating the saponified refined xanthophyll concentrate with an organic or inorganic acid; adjusting the pH between 4 and 7; forming a third refined acidic xanthophyll concentrate and a third aquous phase containing impurities; separating the third refined acidic xanthophyll concentrate from the third aqueous phase; eliminating any excess of acid and any salts formed from the third refined acidic xantophyll concentrate; and extracting the remaining impurities from the refined acidic xanthophyll concentrate with hexane to obtain a highly pure refined xanthophyll concentrate.

10. A process according to claim 1, further comprising saponifying the refined xanthophyll concentrate with a strongly alkaline aqueous solution to obtain a saponified refined xanthophyll concentrate, and isomerizing the saponified refined xanthophyll concentrate to zeaxanthin to obtain a highly pure zeaxanthin-predominant refined xanthophyll concentrate.

11. A process according to claim 1, further comprising saponifying the refined extract with a strongly alkaline aqueous solution to obtain a saponified refined xanthophyll concentrate and isomerizing the saponified refined xanthophyll concentrate, into zeaxanthin to obtain a highly pure, zeaxanthin-predominant xanthophyll concentrate comprising mainly trans-lutein and trans-zeaxanthin.

12. A process according to claim 1, wherein the treatment with a dilute alkali and a dilute acid is carried out under agitation and at a temperature from about 25° C. to 90° C., for a period of about one minute to 4 hours.

13. A process according to claim 1, wherein the treatment with the dilute alkali and dilute acid is carried on under agitation at a temperature of about 40° C. and for a period of about 30 minutes.

14. A process to obtain refined xanthophyll concentrates of high purity starting from plant extracts, comprising: refining the plant extracts by treatment with a diluted aqueous alkaline solution forming a first oleoresin phase and a first aqueous phase containing impurities; separating the first oleoresin phase from the first aqueous phase containing impurities; treating the first oleoresin phase with a diluted aqueous organic or inorganic acid; forming a second oleoresin phase and a second aqueous phase containing impurities; separating the second oleoresin phase from the aqueous phase to obtain a refined xanthophyll concentrate; saponifying the refined xhanthophill concentrate with a strongly alkaline aqueous solution to obtain a saponified refined xanthophyll concentrate; diluting the saponified refined xanthophyll concentrate in water; treating the saponified refined xanthophyll concentrate diluted in water with a diluted organic or inorganic acid to adjust the pH between about 4 to 7; forming a third acidic refined xanthophyll concentrate and a third aqueous phase containing impurities to obtain an acidic refined xanthophyll concentrate; separating the third acidic refined xanthophyll concentrate from the third aqueous solution; eliminating any excess of acid and any salts formed, from the acidic refined xanthophyll concentrate by means of aqueous rinses; separating and drying a purified refined xanthophyll concentrate; and extracting any remaining impurities from the purified refined xanthophyll concentrate with hexane to obtain a highly pure refined xanthophyll concentrate.

15. A process according to claim 14, wherein each of the refining steps with the diluted aqueous alkaline solution and the diluted aqueous organic or inorganic acid, comprises rinsing the oleoresin phase to remove impurities and undesirable components.

16. A process according to claim 14, wherein the aliphatic hydrocarbon is hexane.

17. A process according to claim 16, comprising recovering the hexane for reuse.

18. A process according to claim 14, wherein the xanthophyll concentrates having a concentration of about 98% of xanthophylls, according to the AOAC, and a purity above 95% by HPLC.

19. A process according to claim 14, wherein the purity of the highly pure refined xanthophylls concentrate is above 95%.

20. A process according to claim 14, wherein the aliphatic hydrocarbon extracts the impurities of a non-polar nature.

21. A process according to claim 14, wherein the treatment of the saponified refined xanthophyll concentrate by means of an acid is carried out by diluting the saponified refined xanthophyll concentrate in water, at a ratio of soap:water of about 1:3, at a temperature from about 40° C. to 60° C., and for a period of about 1 to 60 minutes under agitation, to separate an aqueous phase and an acidic refined xanthophyll concentrate phase; rinsing the acidic refined xanthophyll concentrate phase with water to remove acid residues and impurities, and separating and drying the purified refined xanthophyll concentrate.

22. A process according to claim 14, wherein the aliphatic hydrocarbon extraction step is carried on at room temperature or higher, and with a ratio of aliphatic hydrocarbon:xanthophyll concentrate of about 1:1 to 10:1.

23. A process according to claim 14, comprising filtering, centrifuging, drying under vacuum, stabilizing, standardizing and forming the xanthophyll concentrate of high purity.

\* \* \* \* \*